United States Patent [19]

Ponstingl et al.

[11] Patent Number: 5,241,368
[45] Date of Patent: Aug. 31, 1993

[54] FIBER-OPTIC PROBE FOR ABSORBANCE AND TURBIDITY MEASUREMENT

[75] Inventors: Michael J. Ponstingl; Walter N. Trump; Robert C. Kessler, all of St. Louis County, Mo.

[73] Assignee: Custom Sample Systems, Inc., St. Louis, Mo.

[21] Appl. No.: 637,807

[22] Filed: Jan. 7, 1991

[51] Int. Cl.$^5$ .................. G01N 21/53; G01N 21/59
[52] U.S. Cl. ................................ 356/436; 250/573; 250/575; 356/440; 356/73
[58] Field of Search .................. 356/73, 342, 436, 440; 250/573, 574, 575

[56] References Cited

U.S. PATENT DOCUMENTS

| | | | |
|---|---|---|---|
| 4,283,146 | 8/1981 | Roussel | 356/445 |
| 4,643,573 | 2/1987 | McLachlan et al. | 356/342 X |
| 4,753,530 | 6/1988 | Knight et al. | 356/73 |
| 4,786,171 | 11/1988 | LeFebre et al. | 356/440 X |
| 4,989,942 | 2/1991 | Koenigsberg et al. | 250/573 X |
| 5,013,928 | 5/1991 | Ikeda et al. | 250/574 |
| 5,035,508 | 7/1991 | Carter et al. | 356/416 |

Primary Examiner—Vincent F. McGraw
Attorney, Agent, or Firm—Paul M. Denk

[57] ABSTRACT

An optical probe apparatus (10) is for testing physical properties of a fluid (F) such as turbidity. The apparatus comprises a probe assembly (16) removably insertable into the fluid. A photometric light source (12) generates light and fiber optic cables (14) transmits light to and from the probe assembly. Light entering the assembly is directed into the fluid, the light being absorbed or scattered by particles in the fluid as it passes therethrough. The amount of remaining light is sensed and a light output from the probe is produced whose intensity is a function of the amount of remaining light. A light detector measures the light output of the probe assembly and produces an indication of the absorbance or turbidity of the fluid.

13 Claims, 2 Drawing Sheets

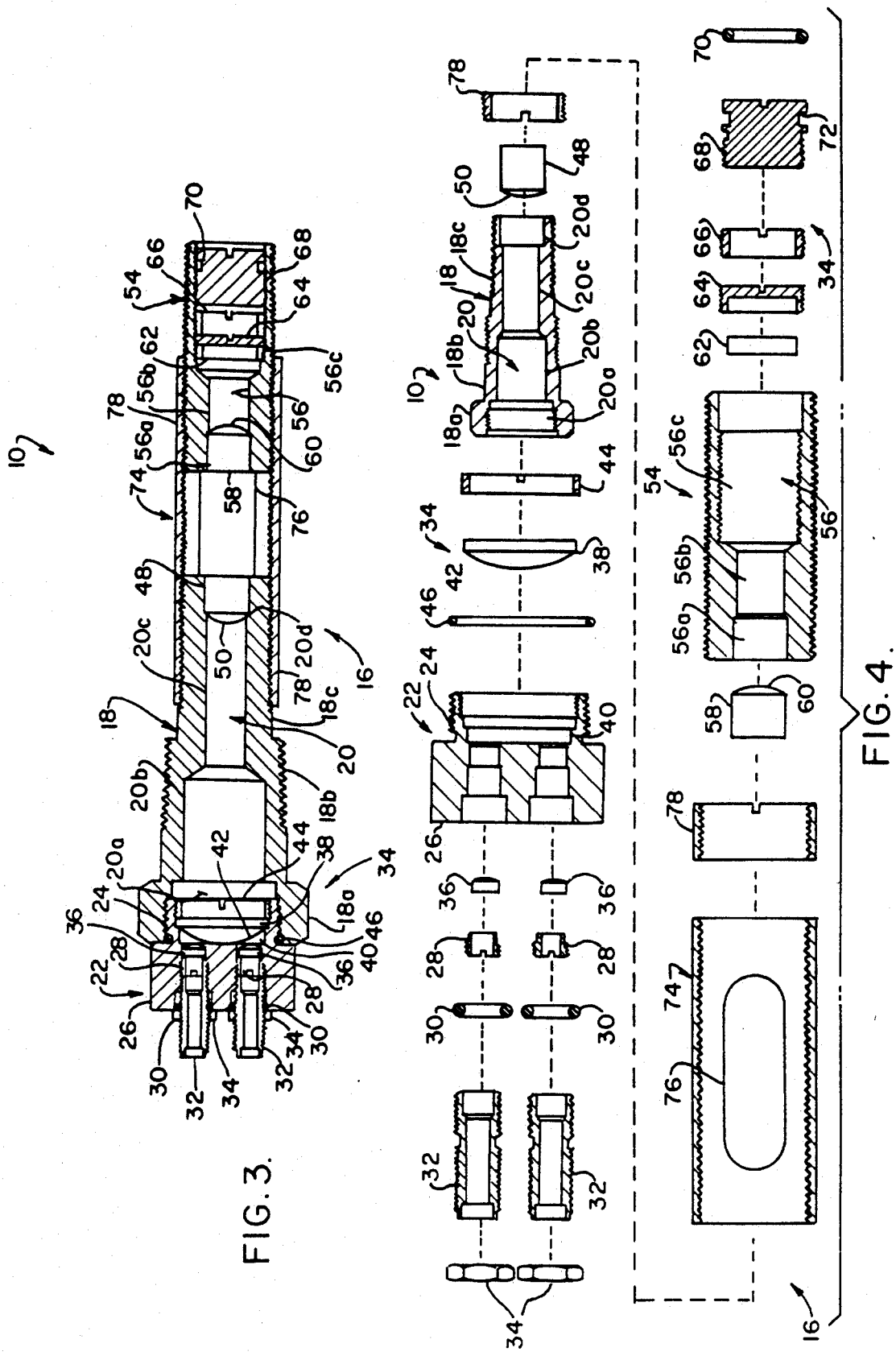

FIBER-OPTIC PROBE FOR ABSORBANCE AND TURBIDITY MEASUREMENT

BACKGROUND OF THE INVENTION

This invention relates to the measurement of fluid absorbance or turbidity in a pipe line carrying a liquid, fluid, or a gas, and, more particularly, to an optical probe capable of use for both absorbance and high and low-range turbidity measurements, and operable in a number of light energy bands (i.e., wavelengths).

The use of optical systems to measure the characteristics of a liquid or gaseous medium flowing in a pipe, or pipeline transmission system, are well-known in the art. See, for example, my U.S. Pat. No. 4,637,730, which is assigned to the same assignee as the present application. It will be appreciated that such systems are adaptable to both laboratory and industrial applications. Further, such systems are usable with fluid mediums which are corrosive, or in which fluid transmission occurs under extreme temperature and/or pressure conditions. A major benefit of such systems is they permit non-invasive testing of the flowing medium. This eliminates the need to draw off samples into some type of extractive holder, and avoids exposure of personnel to the potential harmful effects of the liquid or gas. It also reduces the potential of an explosion due to an inadvertent spark, etc. As disclosed in the U.S. Pat. No. 4,637,730, a light beam is transmitted through opposed transparent windows. The intensity of the received light is compared with that of a reference beam and the amount of attenuation can be used as a measure of, for example, the turbidity of the fluid. U.S. Pat. No. 4,786,171, also discloses a spectral analysis apparatus and method, wherein it includes the transmission of a light path through a sample being measured, with the light path being adjusted to optimize the amount of light absorbed by the sample, and with the absorbance of the sample being calculated from that length in order to provide measurement of the absorbance of the fluid between two different path lengths, within the measuring device.

While the non-invasive system disclosed in our earlier patent does have certain desirable advantages, it is sometimes also advantageous to be able to insert an optical probe into a sample of gas or liquid. In a production process, for example, such a capability eliminates the need to draw a sample off into an extractive sample holder. As before, this eliminates the chance of employees being exposed to the potentially harmful effects of chemicals, as well as the possibility of an explosion.

SUMMARY OF THE INVENTION

Among the several objects of the present invention may be noted the provision of an optical probe for use in testing the physical properties of a liquid or gas enclosed in a container; the provision of such a probe for use in the remote testing of the fluid; the provision of such a probe which is insertable into a fluid stream to facilitate testing so to the eliminate the need for extractive sampling; the provision of such a probe which can be passed through a liquid or gas if the fluid is confined in a container; the provision of such a probe which can be used in laboratory settings, or in industrial processes; the provision of such a probe which is compatible with standard optical cables; the provision of such a probe which is operable in the ultraviolet (Uv), visible, and near infrared (Ir) portions of the light spectrum; the provision of such a probe which can be used as a transmission probe, or as a high or low range turbidity probe; and, the provision of such a probe which can be used in corrossive environments, or in high pressure and/or temperature environments.

In accordance with the invention, generally stated, an optical probe apparatus is for testing physical properties of a fluid such as its absorbance or turbidity. The apparatus comprises a probe assembly removably insertable into the fluid. A photometric light source generates light and fiber optic cables transmit light to and from the probe assembly. Light entering the assembly is directed into the fluid, the light being absorbed by dissolved substances or scattered by particles in the fluid as it passes therethrough. The amount of remaining light is sensed and a light output from the probe is produced whose intensity is a function of the amount of remaining light. A light detector measures the light output of the probe assembly and produces an indication of the absorbance or turbidity of the fluid. Other objects and features will be in part apparent and in part pointed out hereinafter.

BRIEF DESCRIPTION OF THE DRAWINGS

FIG. 3 is a sectional view of a probe assembly used in transmission applications; and, FIG. 4 is an exploded sectional view of the probe assembly.

Corresponding reference characters indicate corresponding parts throughout the drawings.

DESCRIPTION OF A PREFERRED EMBODIMENT

Figure 1:
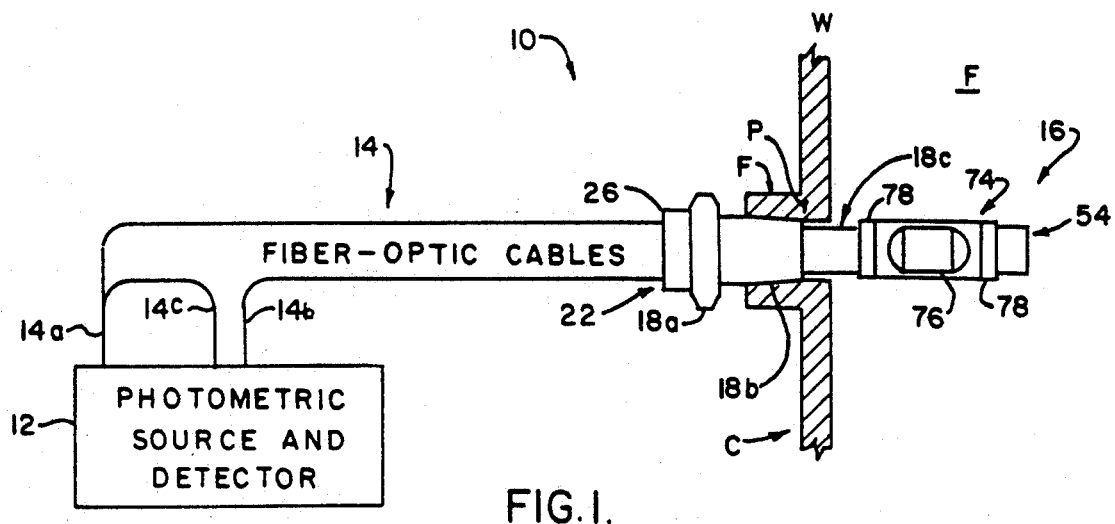
FIG. 1 is a schematic representation of the present invention used to measure the physical properties of a fluid.

Referring to the drawings, apparatus of the present invention is indicated generally 10 in FIG. 1. The apparatus is for use in measuring the turbidity or light transmission characteristics of a fluid F which may be either a liquid, fluid, or a gas. The fluid is enclosed in a container C which may be either a closed container such as is found in a laboratory or plant installation; or a pipeline by which the fluid is transmitted from one place to another. It is a feature of the apparatus that it is usable with many various types of fluids, including corrossive fluids, or fluids under extreme temperatures and/or pressures.

A photometric or light source 12 generates light in one portion of the light spectrum. Preferably, Source 12 generates light in either the ultraviolet (Uv), visible, or near-infrared (Ir) portion of the light spectrum. As seen in FIG. 1, the light source is combined with a light detector. It will be understood, however, that the two could be separate units. The dectector comprises two light-measuring elements, one serving as a reference and the other measuring the light modified by passage through the fluid in transmission applications. In turbidity applications, the reference detector element receives the light scattered by particles in the fluid, and the measuring element receives the light either passed through the fluid or reflected from the window. Light transmission to and from unit 12 is via fiber-optic cables indicated generally 14. In some applications, two such cables, a transmission cable 14a and a return cable 14b are used (see FIG. 2a); while in other applications, a third, turbidity signal cable 14c is also used (see FIGS. 2b and 2c).

Container C has a sidewall W in which is formed an opening P. A probe assembly 16 of the apparatus is removably insertable into the fluid, through the opening. Referring to FIGS. 3 and 4, assembly 16 first includes a generally cylindrically shaped body 18 whose outer diameter varies along its length. The largest diameter portion 18a of the body is at its end which connects with the optical cables 14. Next is an intermediate diameter section 18b the outer surface of which may be threaded as shown or may be adapted to various non-threaded sanitary fittings. This portion of the body is threadably or otherwise sealed in opening P to install the probe in the container and expose it to the fluid. The outer end of the body comprises the smallest diameter section 18c. The outer surface of this section is also threaded for reasons to be described hereinafter.

Body 18 has a longitudinal bore 20 which is axially aligned with the centerline of the body. Bore 20 defines a light path through the body and has a large diameter section 20a at end 18a of the body. The bore then has two succeedingly smaller diameter sections 20b, and 20c respectively. At the outer end of body 18, the right side of the body as seen in FIG. 4, the diameter of the bore slightly increases forming a section 20d. The inner wall of bore section 20a is threaded. A cap 22 has an outer hollow cylindrical section 24. The outer surface of this section is matingly threaded for the section to be received in section 20a of the bore. A plurality of bores 24a, 24b, and 24c extend through head 26 of the cap (see FIGS. 2d-2f), these bores forming ports or terminations for the respective optical cables. A retainer 28 fits in each bore. The bores are sealed against external contamination by an O-ring seal 30. An optical connector 32 fits in each bore and the respective ends of the optical cables are captured by the connector. A nut 34 is threadingly received on each connector to secure the assembly.

Figure 2A:
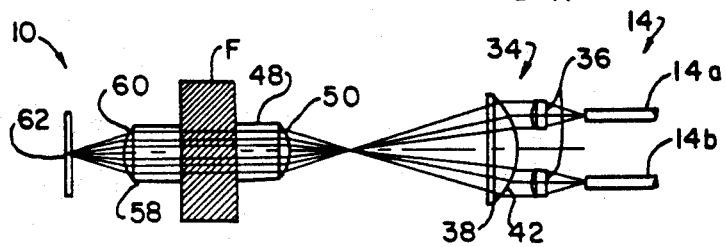
FIGS. 2a-2c are respective schematics of optics used in the probe in a transmission application, a low-range turbidity application, and a high-range turbidity application.
Figure 2D:
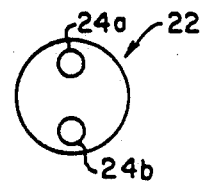
FIGS. 2d-2f are respective end views of the probe connector for the associated applications shown in FIGS. 2a-2c.
Figure 2B:
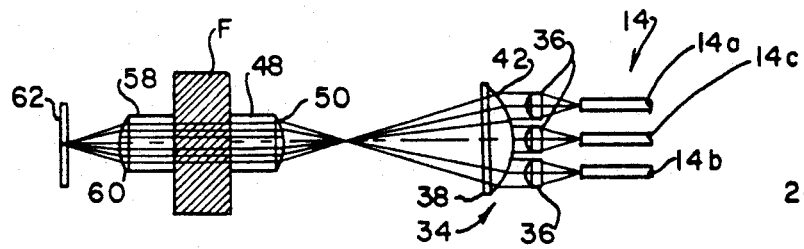
Figure 2E:
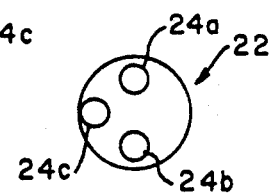

The apparatus includes an optical system indicated generally 34 and this system includes a collimating lens 36 sized to be installed at the inner end of each port and secured by retainer 28. The collimating lens 36 installed in the port to which transmission cable 14a is attached collects the radiant energy emanating from the end of the cable for transmission through the light path defined by bore 20. Similarly, the lens 36 installed in the port to which return cable 14b is attached condenses the radiant energy returning down the path for transmission to the detector portion of unit 12. If a second signal is employed for turbidity measurement, a collimating lens 36 is installed in the port to which cable 14c is attached. An objective lens 38 is mounted in the recessed portion 40 of cap section 24. Lens 38 is inserted into recess 40 so a convex face 42 of the lens faces a convex face of each of the collimating lenses 36. The opposite face of lens 38, as well as the opposite faces of each of the lenses 36, is flat. The function of this set of lenses is to properly focus both the transmitted and return light waves at the ends of the fibers comprising the respective optical cables. As seen in FIGS. 2a and 2b, the light paths of the transmitted, return, and reference light waves are also focused within bore 20 at a point intermediate the ends of the bore. A retainer 44 fits behind lens 38 in the recess to hold it in place. An O-ring seal 46 fits about the outside of section 24 and is sealingly compressed by the end wall of the probe body when the cap is threaded into the end of the body.

Figure 2C:
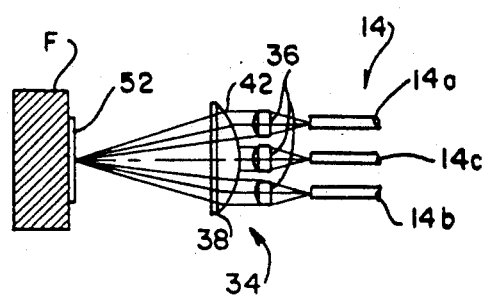
Figure 2F:
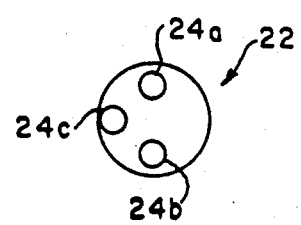

At the opposite end of bore 20, a window lens 48 is fitted into bore section 20d. Lens 48 has a convex face 50 and is mounted in the bore so this face extends back toward the other end of the body. The other face of lens 48 is flat. Alternatively, a separate lens and window assembly may be substituted for lens 48. In this case, the convex lens faces forward. If the apparatus is to be used for high turbidity measurements such as shown in FIG. 2c, a clear window element 52 is installed in this end of the body in place of lens 48. The probe assembly is then inserted into the fluid, the high turbidity level of the fluid, which otherwise inhibits light transmission through the fluid causes light to be reflected back through the window so a turbidity measurement can be made.

For light transmission and low turbidity measurements, the apparatus includes a second body 54 having a longitudinal, axial bore 56 defining a light path. The body has a constant outer diameter (which corresponds to the diameter of section 18c of body 18) and the outer surface of the body is threaded entirely along its length. Bore 56 has a first diameter section 56a adjacent the end of body 54 facing body 18, an intermediate and smaller diameter section 56b, and a third and largest diameter section 56c at its opposite end. A window lens 58 which is substantially identical to lens 48 is installed in bore section 56a, the convex face 60 of the lens facing back into the body. As described for lens 48, an assembly of separate lens and window may be substituted for window lens 58. A mirror 62 is sized to fit in a holder 64. The outer diameter of the holder conforms to that of bore section 56c for the mirror to be installed in this section. A lock ring 66 fits in section 56c behind the mirror holder. The mirror reflects impinging light back along the light path defined by bore 56. A plug 68 is insertable into the back end of the section behind the ring. An O-ring 70 fits in a groove 72 formed in the outer surface of the plug to form a seal about the end of the body when the plug is inserted into the end of bore 56. As an alternative to the described assembly of lens 58, mirror 62, holder, lock ring, plug and O-ring, a cube corner reflector may be used. In this case, reflector body 54 has a bore only sufficient to accommodate the cube corner reflector.

Apparatus 10 next includes a hollow, cylindrical sleeve 74 whose inner diameter corresponds to the outer diameter of section 18c of body 18 and the outer diameter of reflector body 54. The inner face of the sleeve is threaded along its entire length The sleeve has opposed longitudinally extending apertures or slots 76, one of which is shown in the drawings. The sleeve also has associated locking rings 78 which are of the same inner and outer diameter as the sleeve, are internally threaded, and which fit on the respective bodies 18 and 54 to lock the sleeve in place when it is installed. During assembly, a locking ring 78 is threaded onto section 18c of body 18. Next, one end of sleeve 74 is threaded onto the section. Then, body 54 is threaded onto the other end of the sleeve; and, finally, the other locking ring is threaded onto body 54.

The sleeve defines a light path between bodies 18 and 54. The length of this path depends upon the extent to which the sleeve is threaded onto the respective bodies. Further, the apertures permit fluid to flow through the sleeve, with the volume of fluid present in the sleeve also being a function of the extent to which the sleeve is threaded onto the bodies. As shown in FIG. 1, the amount sleeve 76 can be fitted onto the ends of the bodies is such that the ends overlap the ends of the apertures. As shown in FIGS. 2a and 2b, the window lenses 48 and 58 cause the respective incident, reflective, and reference waves to travel in parallel through the fluid so as not to interact with the other. On the mirror side of the probe assembly, the lens 58 also focuses the incident wave on the mirror. Thus, a light wave transmitted by source 12 is directed through the fluid, and is reflected by the mirror back toward the transmission end of the assembly. The light wave passes through the fluid twice, and its intensity is diminished by the absorption or scattering effect of the particles in the fluid. By properly focusing the incident and reflected waves, they pass through the fluid parallel to each other or separate paths, and therefore do not interfere with each other. This enhances the accuracy of the resultant turbidity measurement.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. An optical probe apparatus for testing the physical properties of a fluid for one of absorbance and turbidity, comprising, a photometric apparatus including a light source and a multi-channel detector, a probe assembly insertable into the apparatus and exposed to the fluid being tested, the probe assembly being exposed to the fluid being tested as it passes through the assembly, said probe assembly including a body having a longitudinal bore therein and defining a space for transmission of the light from the light source therethrough, said body having inner and outer ends, said body of the probe assembly having an aperture therein for passing of the fluid therethrough, and said probe assembly provided for receiving the light from the light source and passing it axially of the said assembly and through its aperture and perpendicular to the fluid passing through the body of the probe assembly, said photometric apparatus having a detector therein, said photometric apparatus passing said light from the light source through the body of the probe assembly and its passing fluid and returning said light to the detector after modification of the transmitted light as a result of exposure to the fluid, a light measuring means operatively associated with the photometric apparatus and for producing an indication of the physical properties of the fluid as a function thereof, at least a pair of fiber optic cables extending between the light source, the detector, and the probe assembly, the light source and detector being operable in more than one light wave length of the light spectrum, an optical means provided in the probe assembly and its body, at least a pair of parallel arranged collimating lenses and an aligned objective lens provided for orientation of the transmitted light during its transmission through the body of the probe assembly, a pair of window lens, one of each widow lens provided to either side of the aperture through the body of the probe assembly to provide for parallel rays of light to pass through the probe assembly aperture while being exposed to the fluid therein, a reflecting mirror provided within the outer end of the probe assembly for directing the light passing through the fluid for reflection back through the body of the probe assembly and its lenses and to the detector of the photometric apparatus for analysis, wherein the photometric apparatus emitting the light source receives the modified light passing through the fluid by way of the fiber optic cables and processing the received light for determining the effects of the fluid upon it and for determining the fluid characteristics.

2. The apparatus of claim 1 wherein the probe assembly further includes a cap fitting over one end of the body.

3. The apparatus of claim 2 wherein the cap has a recessed axially aligned within the bore, and the optical means further includes the collimating lenses being parallel arranged within said cap, and axially aligned with the objective lens arranged within the recess of the said cap, so that lenses cooperating with the window lens and mirror for focusing the transmitted and returned light to the ends of the fiber-optic cables.

4. The apparatus of claim 3 wherein the cap further has two spaced apart connector ports extending through the cap to the inner end of the body recess, each port having a columinating lens installed therein for transmitting light, and the light transmitting means communicating with the pair of optical cables, one end of each being received in one of the respective ports, the cables being used for light transmission to and from the light generating means and the light measuring means for light transmission and effecting low-range turbidity measurements to be made during use of the assembly.

5. The apparatus of claim 3 wherein the cap has a third port with a collimating lens installed therein, a third optical cable being connected to the port providing a scattered light signal for the transmission of light through the probe when turbidity measurements are being made.

6. The apparatus of claim 4 wherein the probe assembly further includes a second body.

7. The apparatus of claim 6 wherein the second body has a longitudinal bore defining a light path through the body and the optical means includes said mirror installed at one end of the bore for reflecting light back down a light path.

8. The apparatus of claim 7 further including a hollow sleeve interconnecting the first and second bodies.

9. The apparatus of claim 8 wherein the outer surface of the respective bodies is threaded as is the inner surface of the sleeve whereby ends of the respective bodies are respectively threadably received in the ends of the sleeve.

10. The apparatus of claim 8 wherein the light paths in the respective bodies are axially aligned when the bodies are connected to the sleeve for the overall light path of the assembly to include the sleeve, the length of the light path defined by the sleeve being adjustable to the extent by which the sleeve is threaded onto each of the bodies.

11. The apparatus of claim 10 wherein the sleeve has opposed openings in the sidewall thereof for fluid to flow through the sleeve and the portion of the overall light path defined thereby, particles in the fluid absorbing and scattering the transmitted light.

12. The apparatus of claim 10 further including a window lens means installed in each body at the end of its respective light path adjacent the portion of the overall light path defined by the sleeve, the window lens means effecting a parallel path through the fluid of the incident and reflected light waves.

13. The apparatus of claim 1 wherein the optical means includes a cube corner retroreflector by which light passing through the fluid is directed back to the detector.

* * * * *